(12) United States Patent
Jha et al.

(10) Patent No.: US 7,236,559 B2
(45) Date of Patent: Jun. 26, 2007

(54) DUAL ENERGY SCANNING PROTOCOLS FOR MOTION MITIGATION AND MATERIAL DIFFERENTIATION

(75) Inventors: Sanjay Kumar Jha, Brisbane, CA (US); Souma Sengupta, Foster City, CA (US); Deborah Joy Walter, Burnt Hills, NY (US)

(73) Assignee: General Electric Company, Schenectady, NY (US)

( * ) Notice: Subject to any disclaimer, the term of this patent is extended or adjusted under 35 U.S.C. 154(b) by 45 days.

(21) Appl. No.: 11/205,556

(22) Filed: Aug. 17, 2005

(65) Prior Publication Data

US 2007/0041490 A1  Feb. 22, 2007

(51) Int. Cl.
*A61B 6/00* (2006.01)
(52) U.S. Cl. .............................. 378/5; 378/8; 600/428
(58) Field of Classification Search ................ 378/4, 378/5, 8, 10, 16, 95, 15; 600/425, 428
See application file for complete search history.

(56) References Cited

U.S. PATENT DOCUMENTS 6,643,536 B2 * 11/2003 Nicolas et al. .............. 600/428

2004/0136490 A1 * 7/2004 Edic et al. ..................... 378/4
2004/0136491 A1   7/2004 Iatrou et al.

FOREIGN PATENT DOCUMENTS

WO  WO 2004/008943 A2  1/2004
WO  WO 2004/008967 A1  1/2004

* cited by examiner

*Primary Examiner*—Courtney Thomas
(74) *Attorney, Agent, or Firm*—Armstrong Teasdale LLP (57) ABSTRACT

A method for reducing mis-registration during multiple energy scanning on computed tomographic (CT) imaging systems or multiple energy electron beam tomographic (EBT) systems includes scanning a portion of a patient including a cyclically moving body part using a multiple energy computed tomographic (CT) imaging system or multiple energy electron beam tomographic (EBT) system having at least two different energies, monitoring the cyclically moving body part, and gating the multiple energy CT imaging system or multiple energy EBT system in accordance with the monitored cyclically moving body part so that acquisitions are acquired at at least two different kVps. The data acquired at the different kVps are then utilized to generate material decomposition images of the cyclically moving body part.

20 Claims, 9 Drawing Sheets

DUAL ENERGY SCANNING PROTOCOLS FOR MOTION MITIGATION AND MATERIAL DIFFERENTIATION

BACKGROUND OF THE INVENTION

This invention relates generally to methods and apparatus for detection and diagnosis of abnormalities related to an ischemic heart, and particularly to methods and apparatus for detecting abnormalities related to lack of adequate blood flow to myocardial tissue. However, the methods and apparatus described herein can be used for motion mitigation and material differentiation in any organ or other object, living or non-living, that can be imaged using a plurality of radiation energies and that has a predictable, periodic motion.

Heart disease is the number one cause of mortality in the US. The prevalence of heart disease is also growing in the rest of the world. Most common forms of heart disease that lead to debilitating events are ischemic heart disease, which is due to abnormalities in the structure of the heart's muscle (myocardium) and valves and abnormalities of the cardiac electrical system (arrhythmias).

Atherosclerotic coronary artery obstruction and arterial stenosis are the most common forms of coronary artery disease. It is known that atherosclerosis begins early in life and typically progresses until clinical symptoms occur late in the disease. Coronary calcium can be quantified to assess coronary heart disease risk and to study the progression of atherosclerotic plaque in the coronary arteries. Several studies have shown that coronary calcium can be detected and quantified by Electron Beam Computed Tomography (EBCT) and multi-slice Computed Tomography (CT). However, it is difficult to use current technology to identify and characterize different types of plaque, such as soft plaque and intermediate plaque.

In patients with high risk of Coronary Artery Disease (CAD), as determined by the amount of coronary calcium, visualization of epicardial coronary arteries is necessary to confirm the presence and severity of CAD. Coronary angiography is a standard method for diagnosis of CAD and evaluation of coronary artery bypass graft patency. Coronary angiography was originally developed during the late 1950's and provides excellent resolution for coronary artery visualization. However, coronary angiography is catheter-based and requires direct injections of contrast media into the coronary arteries via a long catheter. Thus, although coronary angiography is a useful method for its intended purposes, there are definite risks of complications involved in its use.

During the past several years, CT Angiography (CTA) and Electron Beam Angiography (EBA) have been developed to replace invasive Coronary Angiography with a less invasive approach involving a simple intravenous injection of a contrast agent. The contrast agent is necessary to provide reliable visualization of long coronary artery segments and high image quality, which themselves are necessary for evaluation of the lumen of vessels and bypass grafts, stenosis detection, and other clinical applications of noninvasive coronary angiography.

Electron Beam Tomography (EBT) and Multi-Slice CT have been shown to be adequate for visualization of the epicardial coronary arteries and detection of stenoses after intravenous injection of contrast agent. However, coronary artery calcification occurring in the intima of vessel walls can interfere with the interpretation of test results. For example, dense calcium spots in the artery wall may cause artifacts that inhibit detection of less dense contrast enhanced coronary lumen and may cause artifacts that might make a correct interpretation more difficult. Also, intracoronary stents can interfere with the assessment of coronary lumen at the site of stent implantation. Furthermore, coronary arteries may respond to plaque growth by either outward expansion of the vessel wall (positive remodeling) or vessel shrinkage (negative remodeling). Some evidence suggests that, while positive remodeling may be partially advantageous (providing benefit in terms of avoiding luminal stenosis), it is also harmful in that marked compensatory remodeling may make the plaque more vulnerable to rupture. In contrast, lesions with negative remodeling may be associated with higher grade stenoses but may appear more stable. Thus, accurate visualization of the arteries and separation from plaque is very important for the study of this pathology.

Some known current cardiac exams include a coronary calcium screening to evaluate the risk of CAD followed by a CT angiography for high-risk patients to evaluate the lumen of coronary arteries. The angiography can be acquired with multiple phases of acquisition at end systole to evaluate wall motion and other cardiac functions. In addition, another known protocol which is known as the "FLEXPHASE™ protocol" can be used. For example, in the FLEXPHASE™ protocol used in the General Electric Company E-SPEED™ computed tomography imaging platform, triggering times are adapted to center the acquired phases at end systole and end diastole. The FLEXPHASE™ protocol allows physicians to capture images when needed, at any point or points in the R-to-R interval, and can be used to visualize coronary arterial motions and to assess cardiac functions, such as ejection fraction. An advantage of the FLEXPHASE™ protocol is that these procedures can be performed at a lower radiation dose than is used by other known protocols.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm. In some CT imaging systems, imaging is synchronized with an electrocardiogram (ECG or EKG) signal monitoring the patient, so that images representing the same phase of the patient's cardiac cycle can be taken during different cardiac cycles. The FLEXPHASE™ protocol described above uses an ECG signal to adapt triggering times for imaging to center the acquired phases at end systole and end diastole, for example.

In spite of recent advancements in CT technology such as faster scanning speed and larger coverage with multiple detector rows, CT still provides only limited characterization of tissue density and composition. Using an x-ray source with a broad energy spectrum, the measured value of the attenuation of any given material is the product of its density and mass attenuation coefficient. A highly attenuating material with low density can result in the same CT number in the image as a less attenuating material with high density. Thus, the two materials can be indistinguishable from one another.

Also, mass attenuation material properties are strongly and non-linearly dependent on the incident x-ray photon energy. This physical phenomenon creates image artifacts that may be exhibited as non-uniformity, shading and streaks. Beam hardening correction algorithms can help compensate for the energy dependent attenuation and mitigate these artifacts, but not completely. In general, known methods to correct for energy dependent beam hardening artifacts fall into two classes: (1) water calibration, in which each CT machine is carefully calibrated to remove beam hardening from materials similar to water, or (2) iterative bone correction, in which bones are separated in a first-pass image, following which, beam hardening from bones is corrected in a second-pass. Nevertheless, beam hardening from materials other than water and bone, such as metal and contrast agent, is difficult to correct, so that even when a correction is applied, the accuracy of the CT image data can still be degraded by the beam hardening.

By employing a dual energy scanning protocol in which two scans are taken at a different peak energy, material discrimination in CT imaging can be used to improve differentiation of materials having similar CT number but different material attenuation properties, for example, calcium and iodine. This technique can be used with an appropriate acquisition method to perform a single CT cardiac examination within a breath hold that can take the place of two standard CT exams, one with contrast and one without contrast. A dual energy cardiac protocol can produce more robust calcium scoring and better vessel characterization in cases in which calcified plaque is present in iodinate coronary arteries. However, artifacts resulting from patient motion between the acquisitions at different peak energies can still lead to data inconsistency and misregistration artifacts in resultant images. Cardiac scans in which the coronary arteries move with velocities ranging from 15 mm/s to 114 mm/s are especially subject to such artifacts. Dual kVp techniques also require an increased radiation dose to a patient, relative to some other known diagnostic techniques.

Motion artifacts are a challenge for all cardiac imaging techniques. In particular, dual energy technique motion artifacts are challenging because this protocol requires that two acquisitions be made within a very short time to mitigate the effects of motion. Data inconsistency resulting from patient motion between dual kVp acquisitions is a source for image artifacts. These artifacts can be a problem in cardiac scans in which coronary arteries move with velocities ranging from 15 mm/s to 114 mm/s. Also, known kVp techniques increase the radiation dosage that a patient receives.

BRIEF DESCRIPTION OF THE INVENTION

In one aspect, the present invention therefore provides a method for reducing mis-registration during multiple energy scanning on computed tomographic (CT) imaging systems or electron beam tomographic (EBT) systems. The method includes scanning a portion of a patient including a cyclically moving body part using a multiple energy computed tomographic (CT) imaging system or multiple energy electron beam tomographic (EBT) system having at least two different energies, monitoring the cyclically moving body part, and gating the multiple energy CT imaging system or multiple energy EBT system in accordance with the monitored cyclically moving body part so that acquisitions are acquired at at least two different kVps. The data acquired at the different kVps are then utilized to generate material decomposition images of the cyclically moving body part.

In yet another aspect, the present invention provides a computed tomographic (CT) imaging system or multiple energy electron beam tomographic (EBT) system having a multiple energy x-ray source and detector array configured to scan a portion of a patient including a heart to thereby collect data and to reconstruct material decomposition images of the portion of the patient including the heart utilizing the scanned data. The CT imaging system or multiple energy EBT system also has electrocardiogram (ECG) monitor configured to monitor cardiac phase of the heart to generate an ECG signal representative thereof. The CT imaging system or multiple energy EBT system is configured to gate the multiple energy CT imaging system or multiple energy EBT system in accordance with an ECG signal so that acquisitions of data are acquired at at least two different kVps, and to utilize the acquired data at the different kVps to generate material decomposition images including images of the heart.

It will be seen that configurations of the present invention are useful, for example, in the differentiation of calcified coronary arteries from contrast enhanced vessels, by providing a protocol or protocols that result in minimal mis-registration even for fast moving coronary vessels. Moreover, there is no dose penalty compared to known protocols for cardiac studies. The utility of using one exam to replace two conventional exams will be offset any increase in dose due to the acquisition of two kVp scans.

DETAILED DESCRIPTION OF THE INVENTION

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Technical effects of the present invention include, in various configurations, gating of a CT imaging system to acquire data at particular times and at particular kVps, reconstruction of images using the acquired data, and/or determination of a calcification score for a lumen. These and other technical effects and the manner in which they are accomplished are described below.

Figure 1:
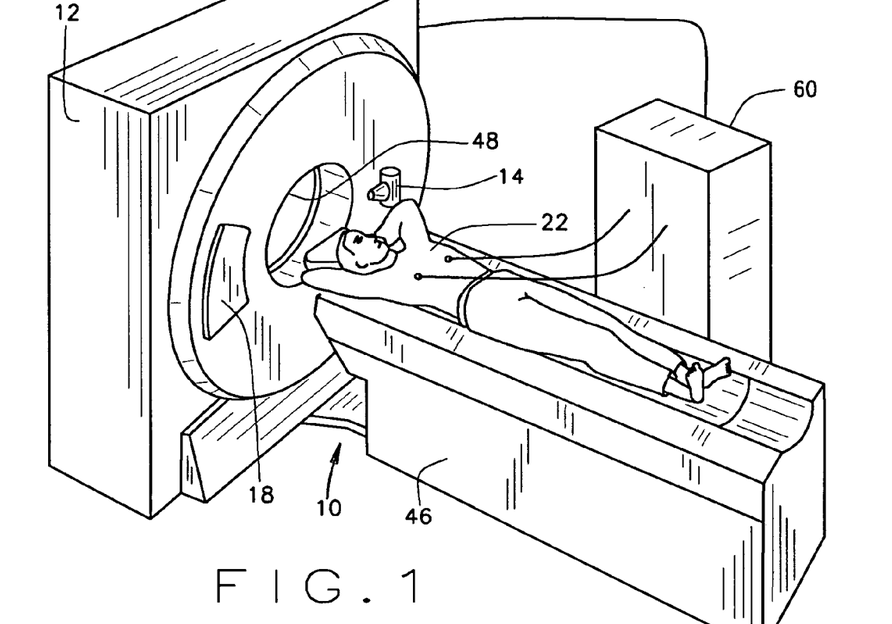
FIG. 1 is a pictorial diagram of a computed tomographic imaging system configuration of the present invention.
Figure 2:
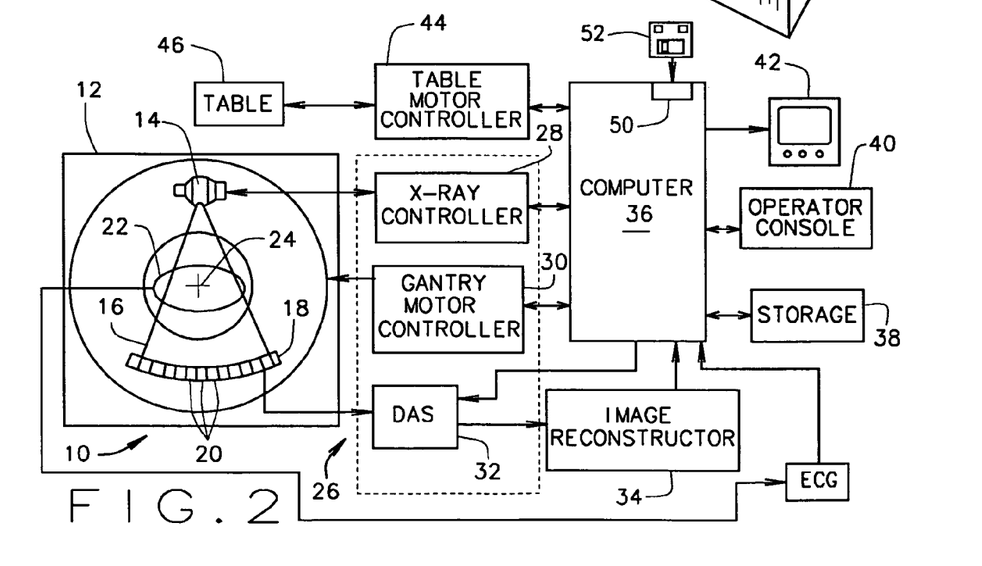
FIG. 2 is a schematic block diagram of the computed tomographic imaging system configuration shown in FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has a radiation source such as x-ray tube 14 (also called x-ray source 14 herein) that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22 between array 18 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube display or other suitable type of display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48. In some configurations, an ECG machine 60 monitors electrical signals indicative of the cardiac phase of patient 22. A signal from ECG machine 60 is used by computer 36 to prospectively gate the operation of imaging system 10 so that times for acquiring data for reconstructing images at particular portions of the cardiac phase of patient 22 are determined. Radiation source 14 is also gated in accordance with the determined times in some configurations of the present invention to thereby reduce the radiation dose to which patient 22 is subjected and to ensure that data at selected kVps is acquired at particular times relative to the cardiac cycle.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to fourth generation CT systems (stationary detector—rotating x-ray source) and fifth generation CT systems (stationary detector and x-ray source), and specifically to electron beam computed tomographic (EBCT) imaging systems. Additionally, it is contemplated that the benefits of the invention accrue to imaging modalities other than CT. Additionally, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

Some configurations of the present invention provide a method and/or an apparatus to minimize misregistration during dual energy scanning on CT or EBCT systems. Benefits of some configurations of the present invention include some or all of increased sensitivity in size of calcified region, increased accuracy in measurement of calcium density, improved visualization of true lumen, better stenosis detection, and/or improved accuracy in measurement of vessel cross section over that which is possible using known methods and apparatus for dual-energy scanning.

In some configurations of the present invention, dual energy for CT imaging is provided using any suitable means for acquiring measurement of x-ray attenuation at two or more energy levels or "bins," although two bins are sufficient in many configurations. Measurements are acquired by changing the incident energy of a monochromatic source, adjusting the incident spectrum by changing the x-ray source maximum potential (kVp), providing k-edge filters before or after the patient, and/or using energy sensitive detectors. Accuracy of the results is a function of the separation or "uniqueness" of the two or more energy bins and the attenuation properties of the materials that are to be differentiated. Once the dual energy data is acquired, analysis takes place before image reconstruction in some configurations, and after reconstruction in others. Decomposition techniques that use the dual energy information in various configurations of the present invention fall into one of three class depending upon on the type of information retrieved. The three general classes of information provided are effective atomic number and density, attenuation due to Compton scattering and electron density, and the physical densities of the two known components.

New information about material composition is available from dual energy techniques because the x-ray absorption linear attenuation coefficient of an element has a unique functional dependence on photon energy. Over the range of x-ray photon energies used in CT, the attenuation coefficient $\mu(E)$ is dominated by two major attenuation processes, namely, the photoelectric effect and Compton scattering. Each of these processes has a fixed and unique functional dependence on energy that can serve as a linear basis set for any material. That is, $$\mu(E) = x\mu_p(E) + y\mu_C(E)$$

where $\mu_p(E)$ is the linear attenuation as a function of energy due to the photoelectric effect and $\mu_C(E)$ is the linear attenuation as a function of energy due to the Compton scattering effect.

A consequence of this relationship is that the energy dependence of the attenuation coefficient of any material can be expressed as a linear combination of that of two other materials. Therefore, each material can be characterized by two density values, $\rho_1, \rho_2$, that are derived from the attenuation measured at two different kVp spectra, $\mu_1(E)$, $\mu_2(E)$. For example, $$\mu(E) = x\mu_p(E) + y\mu_C(E) = \rho_1\mu_1(E) + \rho_2\mu_2(E).$$

Thus, in some configurations of the present invention, these two material density values are used to encode the pixel values apart from or in combination with Hounsfield units. Materials with similar density can thus be differentiated according to average atomic number. Also in some configurations, contrast agents are used with atomic numbers significantly different from materials normally present in the body, as these contrast agents are imaged with high contrast. Furthermore, because the dual energy analysis makes explicit use of the energy dependence of the attenuation, beam hardening artifacts seen in conventional CT are reduced or absent in many configurations of the present invention. Also, the accuracy of CT numbers associated with pixels is not affected by beam hardening corrections when using a dual energy technique. This increased accuracy is to be contrasted with the accuracy of CT numbers associated with pixels obtained using a single energy technique, because the accuracy in this case is adversely affected by beam hardening corrections that must necessarily approximate the energy dependent attenuation with data from a single energy value.

Different methods are used in various configurations of the present invention to obtain dual energy measurements. These methods include:

(1) Scanning with two distinctive energy spectra. In this method, patient motion may occur during the two scans, and there may be a large spectra overlapping area.

(2) Detecting photon energy in accordance with penetration depth at the detector. This method may still result in some overlapping energy spectra, because the stopping of photons is a statistical process.

(3) Counting photons with an energy selective detector.

All three methods are suitable for use in configurations of the present invention, however, the third method advantageously provides a clean spectrum separation and an adjustable energy separation point for balancing photon statistics. Method (1) can be somewhat more difficult to use due to patient motion between two scans and the possibility of a large spectrum overlap. Method (2) may also result in some overlapping energy spectra, because the stopping of photons is a statistical process.

In some configurations of the present invention, "Protocol 1" is used. Protocol 1 provides that a patient be scanned with two separate energy spectra at separate times by, for example, modulating the x-ray peak voltage. Patient motion that occurs during the two scans can potentially be a source of inaccuracies and image artifacts. However, configurations of the present invention significantly reduce mis-registration caused by scanning at two different time as compared to conventional protocols. Some configurations of the present invention use prospective cardiac gating with a prospective triggering technique that adapts triggering times of the CT scanner so that an acquisition always occurs at a point in the cardiac cycle at which there is minimum motion, thus ensuring that the acquisitions for the two kVps occur at least approximately, or at best, exactly at the same, optimum phase of the cardiac cycle. A temporal resolution of 50 ms is used in some configurations of the present invention so that that protocols with two contiguous acquisitions (two different kVps) separated by short setup delay are feasible.

An appropriate protocol can be selected dependent on various parameters such as temporal resolution of the acquisition, patient heart rate, patient's ability to hold breath, etc.

Figure 3:
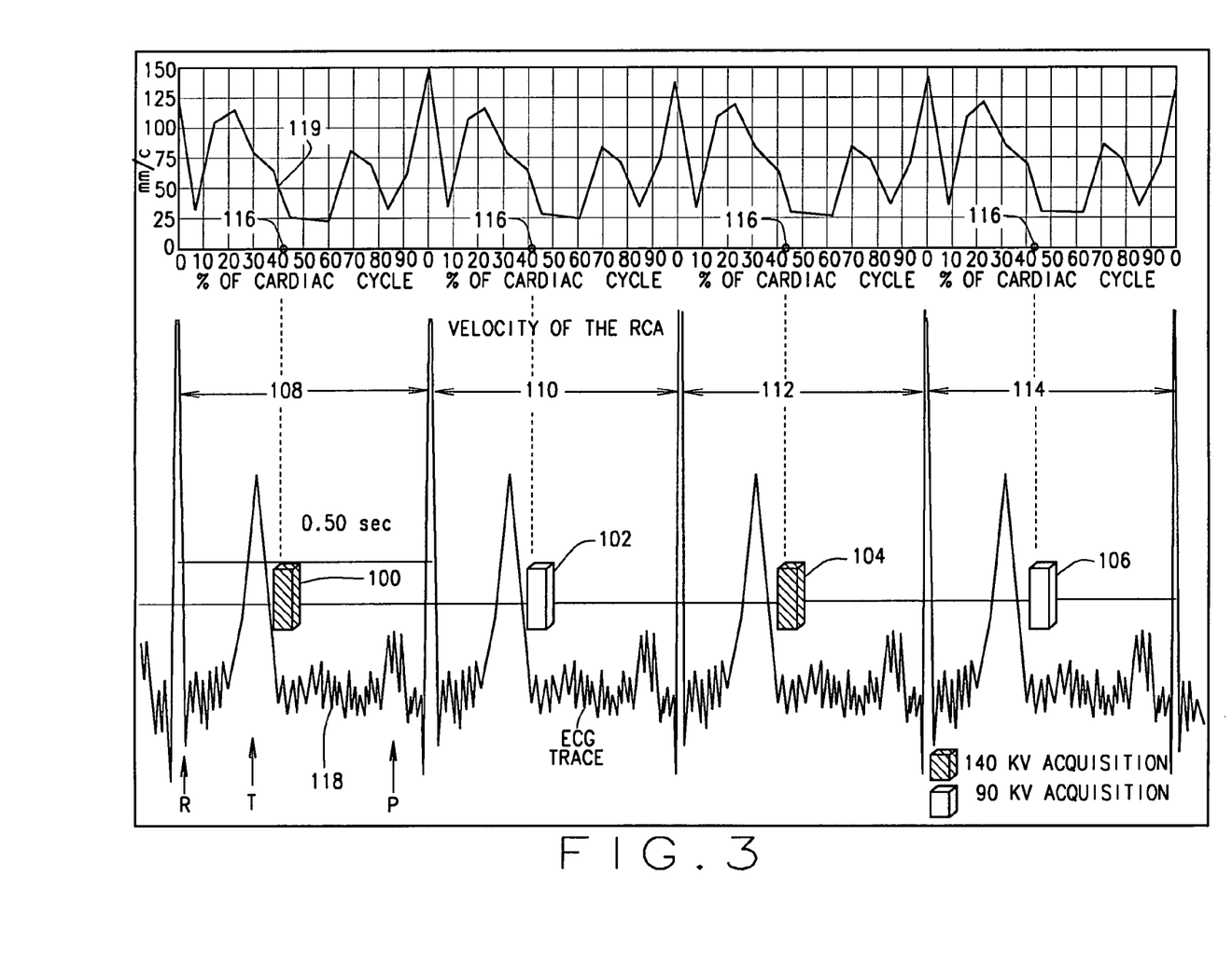
FIG. 3 is a graph illustrating the relationship between data acquisition, kVp applied to the x-ray source of FIG. 1, ECG graph, and lumen movement in a first configuration of the present invention.

For example and referring to FIG. 3, in Protocol 1, a single phase acquisition represented by box 100 at 140 kVp is followed by another single phase acquisition represented by box 102 at 90 kVp. Each kVp acquisition 100, 102, 104, 106 is acquired in a different cardiac cycle 108, 110, 112, and 114, respectively, and prospective cardiac gating with a prospective triggering technique is used to ensure that acquisitions 100, 102, 104 and 106 each begin at the same cardiac phase 116 for both the kVps. ECG machine 60 (shown in FIG. 1) is used to generate ECG signal 118, which is used to generate the triggering or gating signals controlling acquisitions 100, 102, 104, and 106. Corresponding arterial velocity is shown by graph 119, which is aligned with ECG signal 118. The repeatability of the heart motion can be expected to reduce or eliminate scan misregistration. Protocol 1 provides good results for patients who can hold their breath during the data acquisition phase for both kVps. Other configurations of the present invention may be more suitable for patients who cannot hold their breath this long.

Figure 4:
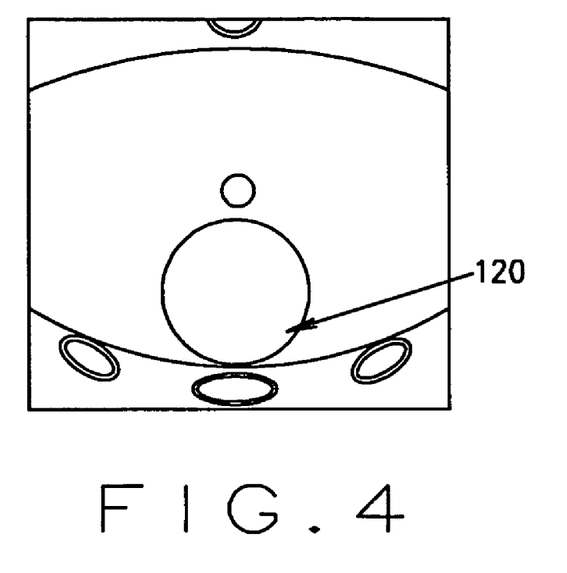
FIG. 4 is an illustration of a simulated cardiac scan at 140 kVp using the acquisition protocol represented by FIG. 3.
Figure 5:
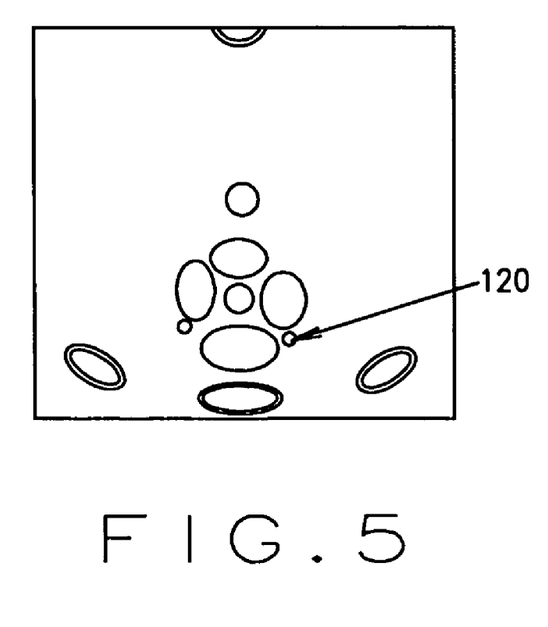
FIG. 5 is an illustration of a simulated water density image reconstructed using the acquisition protocol of FIG. 3 and a basis material decomposition, showing negligible artifacts.
Figure 6:
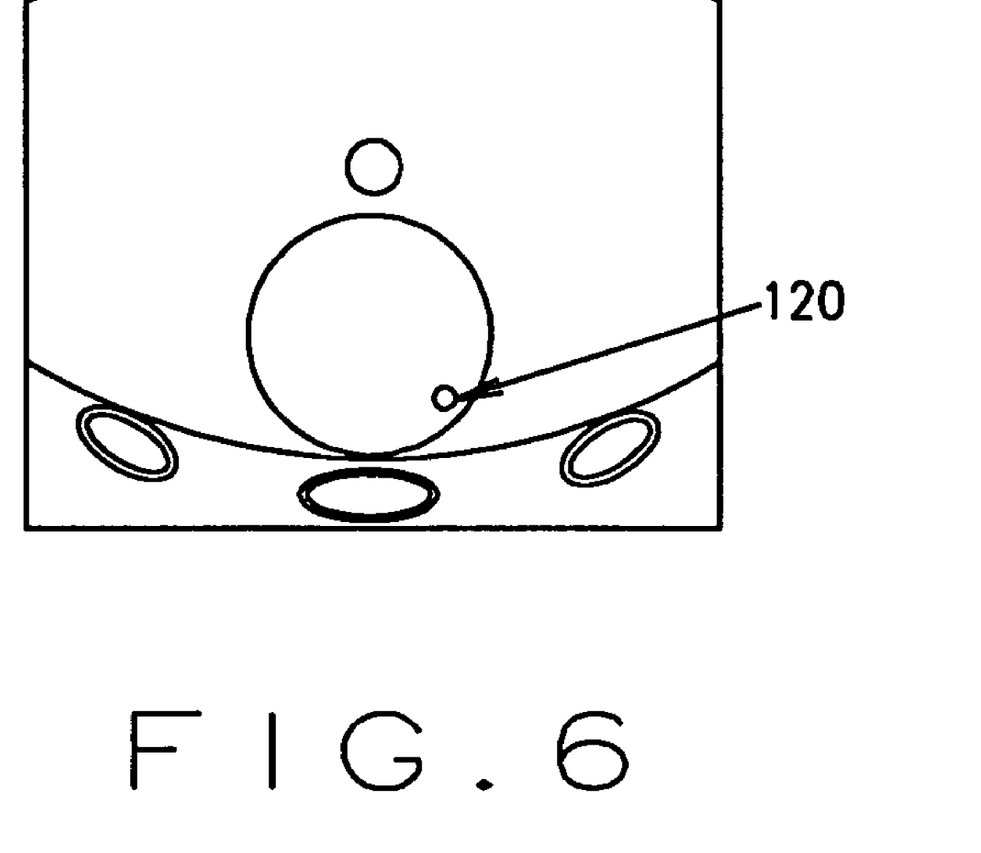
FIG. 6 is an illustration of a simulated iodine density image reconstruction using the acquisition protocol of FIG. 3 and a basis material decomposition, showing negligible artifacts.

Results of a simulation of the protocol described above are shown in FIGS. 4 through 6. A coronary artery 120 being simulated was moved at a simulation speed of 10 cm/sec. Scans were simulated for 90 and 140 kVp. The image of FIG. 4 shows a simulated cardiac scan at 140 kVp. The image of FIG. 5 shows a simulated water density image and the image of FIG. 6 shows a simulated iodine density image. The latter two images were determined using a basis material decomposition, using, for example, the method described above. Artifacts due to misregistration are almost completely absent. Simulated artery 120 was started from the same location, assuming no misregistration, and was moved at the same speed for each scan to simulate arterial motion.

Figure 7:
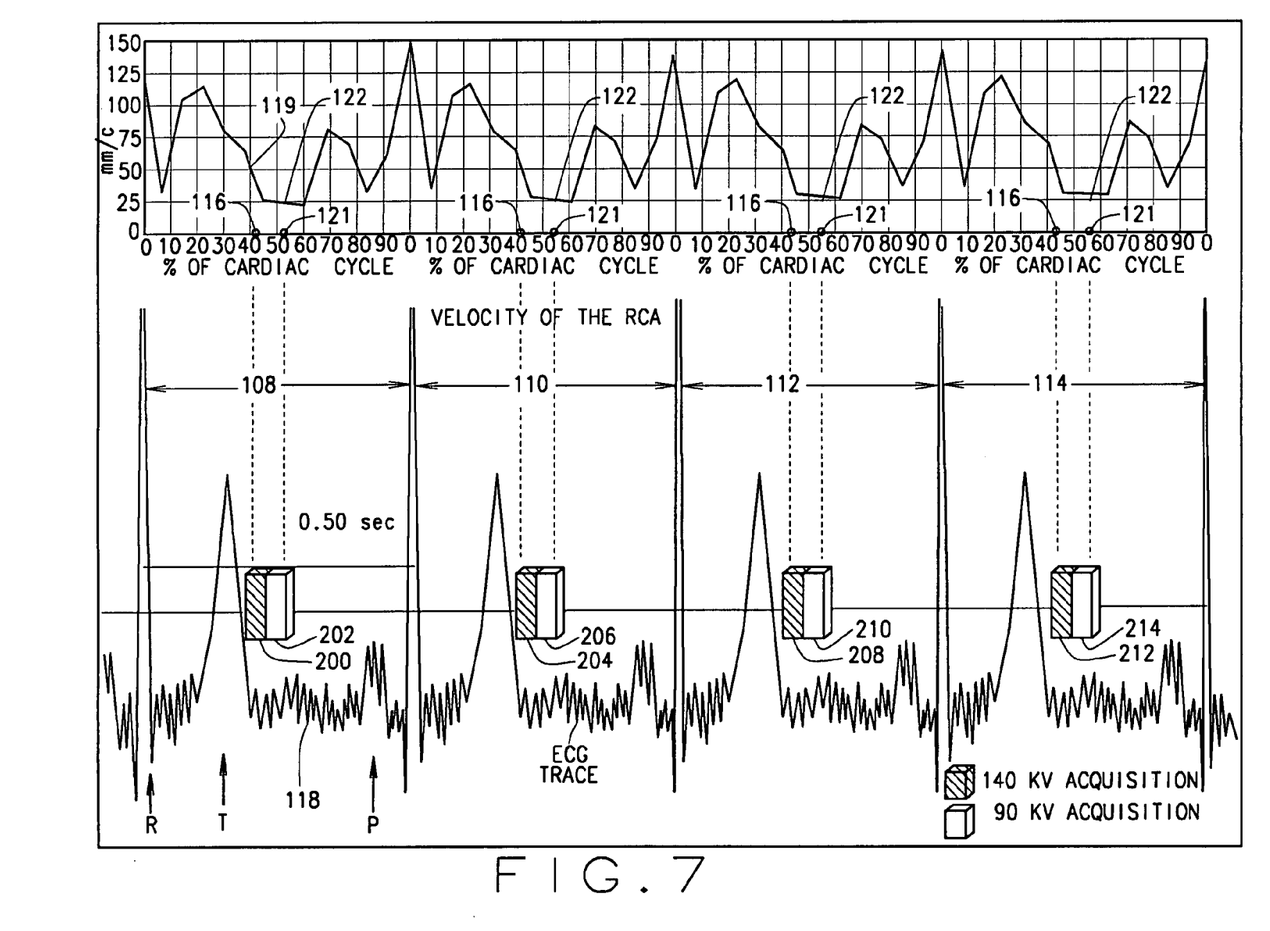
FIG. 7 is a graph illustrating the relationship between data acquisition, kVp applied to the x-ray source of FIG. 1, ECG graph, and lumen movement in a second configuration of the present invention.
Figure 8:
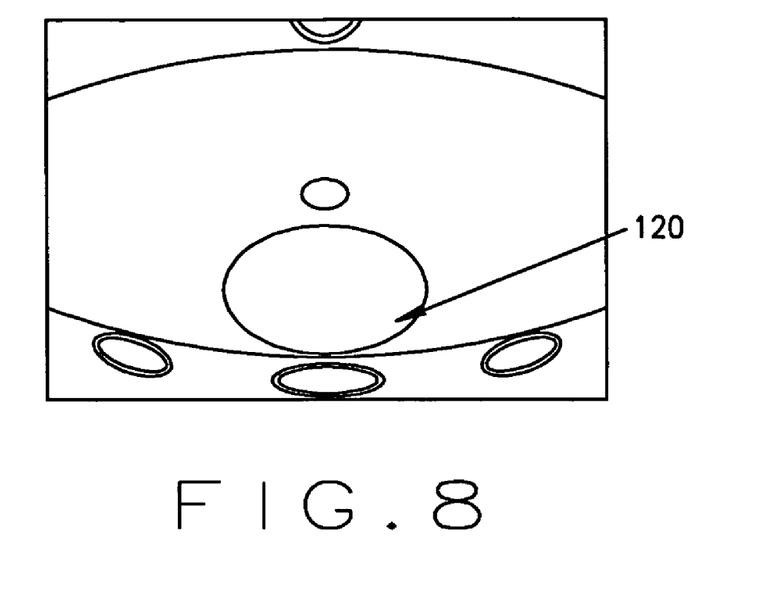
FIG. 8 is an illustration showing a simulated start location for a coronary artery for a 90 kVp scan shown in FIG. 7.
Figure 9:
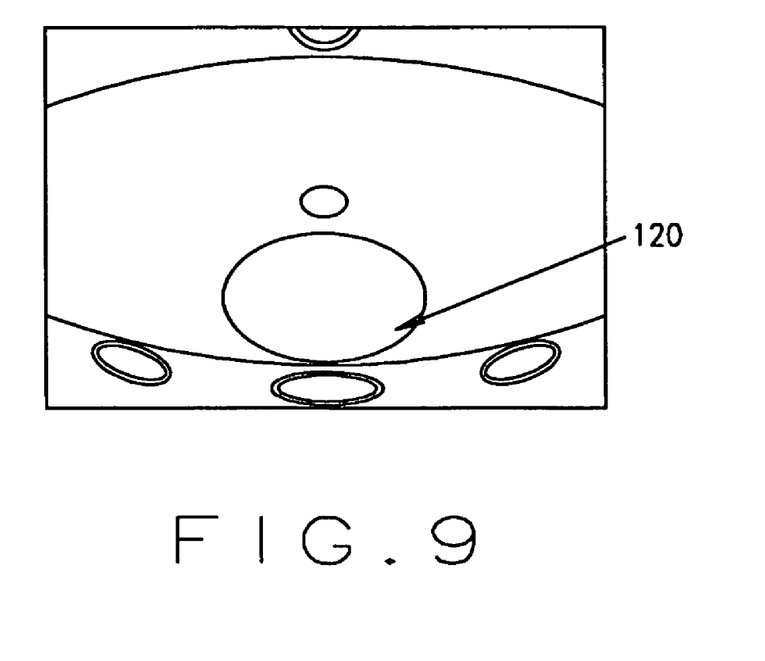
FIG. 9 is an illustration showing a simulated start location for a coronary artery for a 140 kVp scan shown in FIG. 7.

In some configurations of the present invention and referring to FIG. 7, "Protocol 2" is used. In Protocol 2, a single phase data acquisition 200 at 140 kVp is followed immediately by the start of another data acquisition 202 at 90 kVp. Thus, although each pair of data acquisitions 200 and 202 (140 kVp and 90 kVp), 204 and 206, 208 and 210, and 212 and 214 is acquired in the same cardiac cycle 108, 110, 112, and 114, respectively, acquisition for each kVp begins at a slightly different cardiac phase 116 or 121. Each 90 kVp acquisition 202, 206, 210, and 214 starts within 50 ms of a corresponding 140 kVp acquisition 200, 204, 208, and 212, respectively, so any misregistration due to motion during this time is very small. Moreover, acquisitions 200, 202, 204, 206, 208, 210, 212, and 214 are gated in some configurations to take place near or during a period of minimum movement 122. Protocol 2 may be more suitable for patients who have difficulty holding their breath for the period of time needed for Protocol 1.

Figure 10:
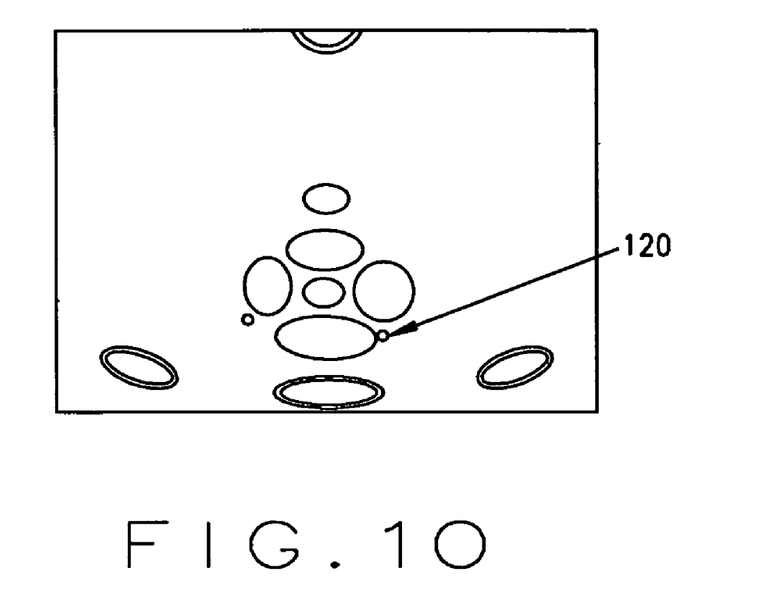
FIG. 10 is an illustration of a simulated water density image reconstructed using the acquisition protocol of FIG. 7 and a basis material decomposition, showing an acceptable level of artifacts produced thereby.
Figure 11:
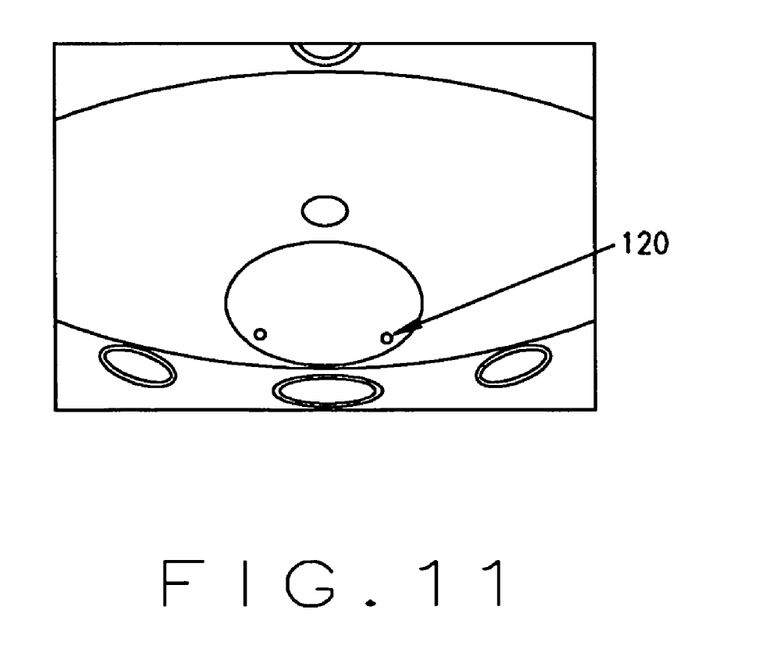
FIG. 11 is an illustration of a simulated iodine density image reconstruction using the acquisition protocol of FIG. 7 and a basis material decomposition, showing an acceptable level of artifacts produced thereby.

FIGS. 8 through 11 show other images from simulation of Protocol 2. In this simulation, a simulated coronary artery 120 was moved at a speed of 10 cm/sec. Scans of data acquisitions were simulated for 140 kVp and 90 kVp in FIGS. 8 and 9, respectively. The simulated start location for coronary artery 120 for the 90 kVp scan shown in FIG. 8 was different than that used for the 140 kVp scan shown in FIG. 9. For purposes of this simulation, it was assumed that artery 120 kept moving at the same speed throughout the simulation, including during the changeover from 90 kVp to 140 kVp (50 ms). The image in FIG. 10 shows a simulated water density image, while the image in FIG. 11 right shows a simulated iodine density image. Some artifacts are caused by a small amount of mis-registration resulting from use of Protocol 2, but these artifacts are considered to be at an acceptable level. Although Protocol 2 does introduce some slight mis-registration, it is a viable option for patients who cannot hold their breath for the length of time required for Protocol 1.

Figure 12:
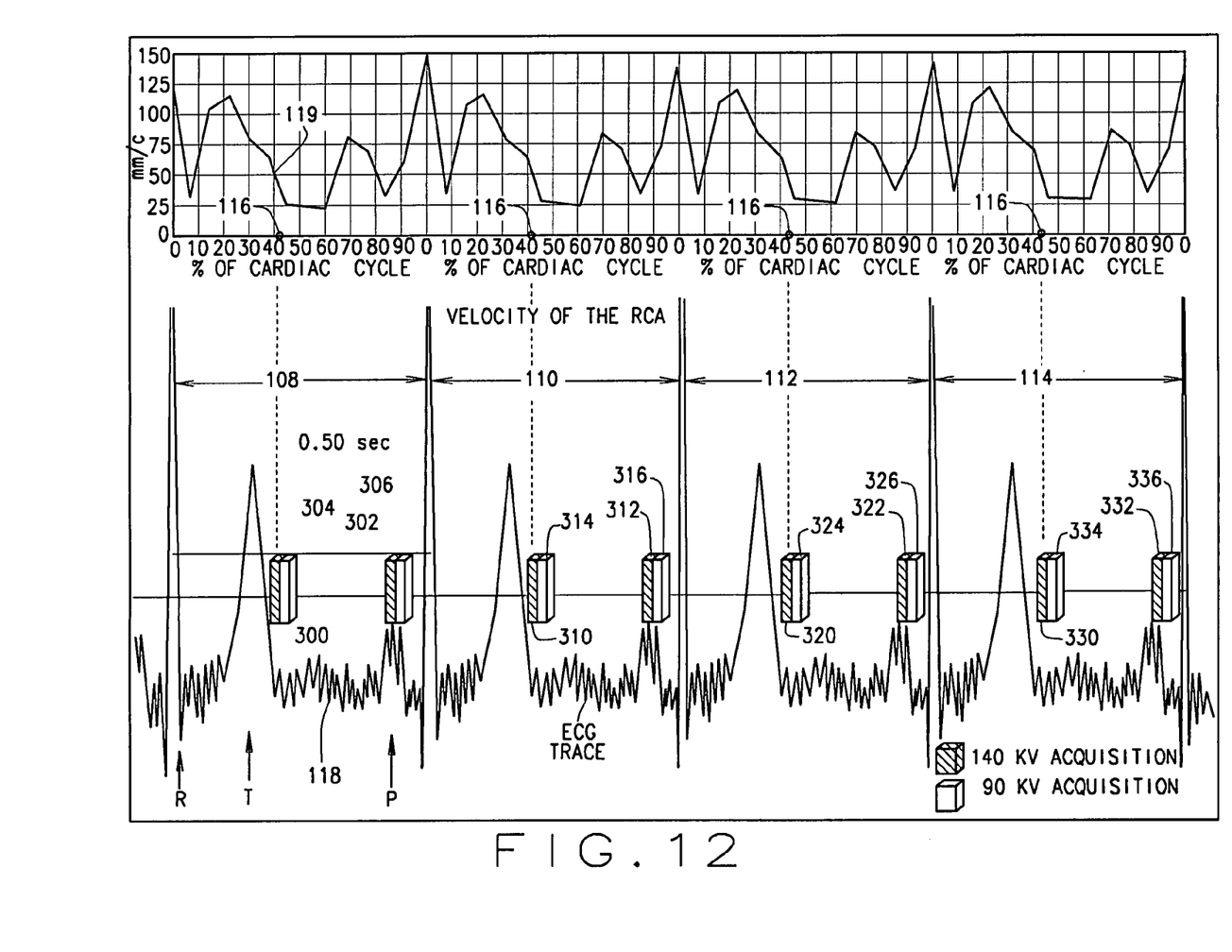
FIG. 12 is a graph illustrating the relationship between data acquisition, kVp applied to the x-ray source of FIG. 1, ECG graph, and lumen movement in a third configuration of the present invention.

In some configurations of the present invention and referring to FIG. 12, "Protocol 3" is used In Protocol 3, two phases are acquired at different kVps in the same cardiac cycle, for example, two phases are acquired at 300 and 302 at 140 kVp and two phases are acquired at 304 and 306 at 90 kVp. Each kVp acquisition is acquired in the same cardiac cycle 108 and the next acquisition begins at a different cardiac phase. (In other cardiac cycles such as 110, 112, and 114, phases corresponding to 300, 302, 304 and 306 are acquired, namely the set 310, 312, 314, and 316, the set 320, 322, 324, and 326, and the set 330, 332, 334, and 336 in the example shown in FIG. 12.) Acquisition 300 of the first 140 kVp data is done near end systole and is followed by an acquisition 304 at 90 kVp. Near end of diastole, another 140 kVp scan 302 is acquired and that scan is followed by acquisition of another 90 kVp scan 306. The time difference between 140 kVp and 90 kVp scans 300 and 302, and between 304 and 306 is less than 50 ms, so any mis-registration is similar in magnitude to that of Protocol 2. In Protocol 3, the patient breathhold is the same as in Protocol 2. Protocol 3 can provide a calcium score, angioram as well as ejection fraction results.

Figure 13:
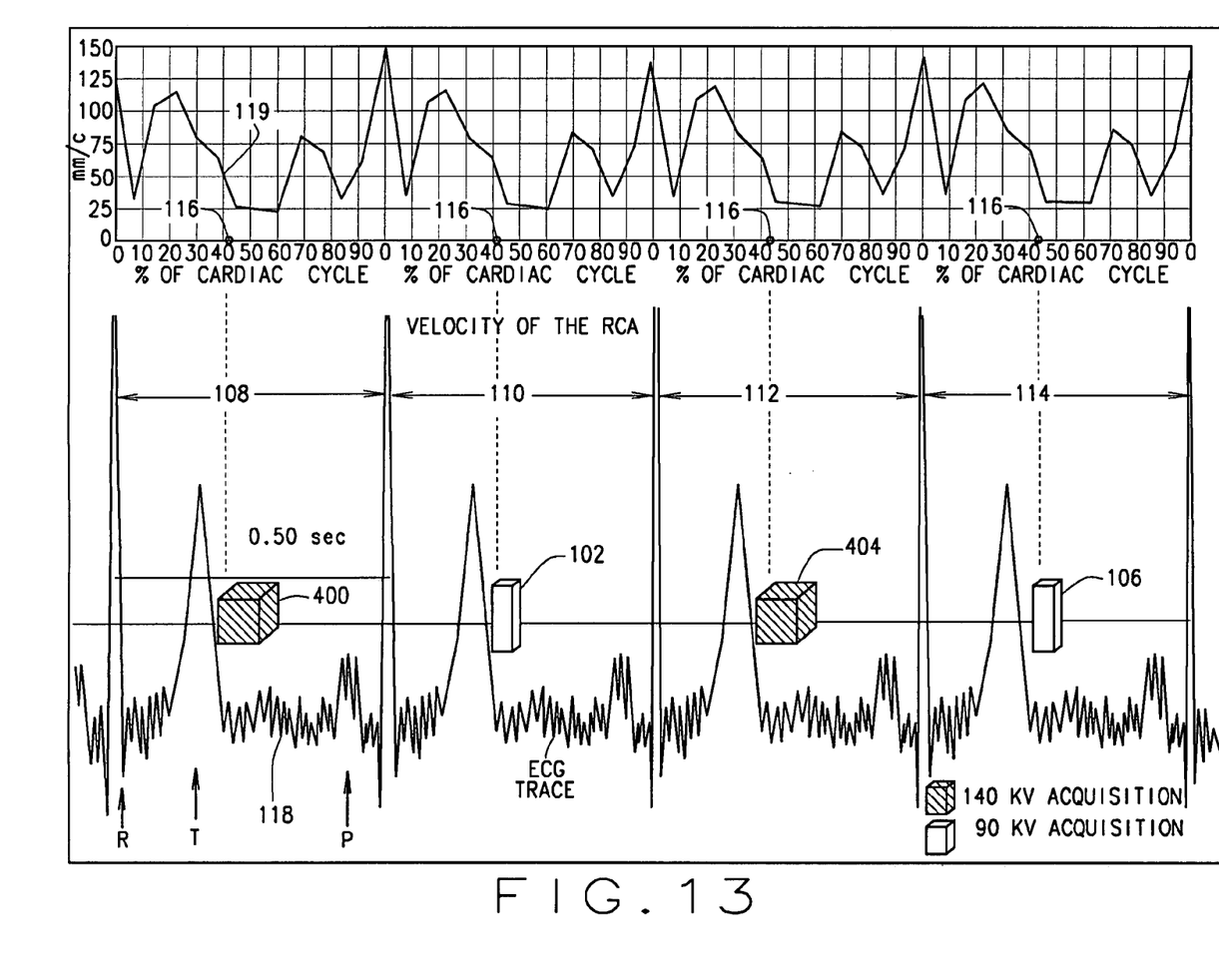
FIG. 13 is a graph illustrating the relationship between data acquisition, kVp applied to the x-ray source of FIG. 1, ECG graph, and lumen movement in a fourth configuration of the present invention.

In some configurations of the present invention and referring to FIG. 13, "Protocol 4" is used. Protocol 4 is a multiphase variant of Protocol 1. Protocol 4 provides a method for taking a full cardiac scan in a single study. In one configuration of Protocol 4, a multiphase acquisition 400 is taken at 140 kVp (instead of single phase acquisition 100 in FIG. 3) followed by a single phase acquisition 102 at 90 kVp. Each kVp acquisition 400, 102, 404, 104 is completed in a different cardiac cycle 108, 110, 112, 114, respectively and acquisition begins at a similar cardiac phase 116 for both kVps. Since the phase is similar, mis-registration is small or minimal. As with Protocol 1, double the usual breath hold is required. However, scanning using Protocol 4 can provide coronary calcium score, angiogram, wall motion and cardiac function results in a single study.

Some configurations of the present invention vary Protocols 1, 2, 3, and/or 4 by changing the scan speed, scan phase location, scanning kVp, etc. from that described above. For example, either or both kVps can be varied from the 140 kVp and 90 kVp described above in connection to the various Protocols. Also, and more generically, a CT imaging system 10 that is used to perform the acquisitions can be a dual-energy CT imaging system or more generally, a multiple energy CT imaging system having two or more x-ray radiation energies, and may be a dual-energy or multiple energy EBCT imaging system. Two different energy scans may also be acquired using different amounts of pre-patient filtration.

Coronary calcium scoring has become ubiquitous as a means of assessing coronary heart disease risk and as means of studying the progression of atherosclerotic plaque in the coronary arteries. The various protocols provided by configurations of the present invention provide sensitive and robust identifications of calcium for coronary calcium scoring in the presence of contrast enhanced vessels. The most common techniques for coronary calcium scoring depend on (a) the area of the calcified lesion and (b) the density of calcium in the lesion. In each protocol, images are generated using material basis function decomposition from the data acquired at the different kVps, so that calcium can be clearly discriminated from other materials. Thus, identification of the calcified lesions is more robust than that obtained by threshholding of CT numbers as in known methods. The density of calcium can also be calculated more accurately and more reliably using the decomposition technique than using CT numbers.

Moreover, it will be appreciated that configurations of the present invention provide better stenosis detection and improved accuracy in measurement of vessel cross section as well as an improvement in visualizations of true lumen and more accurate measurement of cross-section of vessels. More accurate measurement of cross-section is particularly evident when calcified plaque is present next to the vessel e.g. calcium in RCA. Calcified plaques can be identified and registered accurately using configurations of the present invention on an EBCT or CT Scanner and removed in a post-processing technique using resulting images to characterize the vessel. Thus, various configurations of the present invention used in conjunction with material basis function decomposition can result in a better cardiac exam, including improved calcium scoring, improved angiographic study, wall motion and cardiac function, for the same dose as known prior art protocols used currently for similar exams. In some configurations, a full cardiac exam is made possible in one breath hold.

Configurations of the present invention can be used to accurately visualize a true lumen of a vessel even in the presence of calcium, thereby allowing better coronary artery disease detection, and especially stenosis. Moreover, configurations of the present invention increase the accuracy and sensitivity calcium quantification and scoring by combining triggering at an optimum point of the cardiac cycle with high temporal resolution acquisitions at multiple energies.

Acquisitions for the different energies are done at the same phase of the cardiac cycle irrespective of the heart rate in some configurations of the present invention. For example, in some configurations of the present invention, triggering for image acquisition is based on R—R interval length and/or RT segment length for a patient and the temporal resolution of an acquisition. The data acquired thereby using different energies thus has a small or a minimal amount of mis-registration, thus result in minimal artifacts when images are reconstructed. Furthermore, a complete cardiac examination can be performed using configurations of the present invention. Calcium can be quantified and vessel visualized in a single breath hold. Modifications to the protocols described herein can be made in accordance with the heart rate of the patient, the ability of the patient to hold his or her breath, the kind of diagnosis required, etc. Also, configurations of the present invention are not limited to detection of cardiac calcification, but may be used more generally for material/tissue discrimination. (Cardiac calcification determination is regarded herein as one type of material/tissue discrimination.)

Furthermore, although a third generation CT imaging system 10 is recited in example configurations described herein, the invention can be practiced using other generation CT imaging systems. For example, multiple energy electron beam computed tomographic (EBCT) imaging systems can be used.

While the invention has been described in terms of various specific embodiments, those skilled in the art will recognize that the invention can be practiced with modification within the spirit and scope of the claims.

What is claimed is:

1. A method for reducing mis-registration during multiple energy scanning on computed tomographic (CT) imaging systems or multiple energy electron beam tomography (EBT) systems, said method comprising:
   scanning a portion of a patient including a cyclically moving body part using a multiple energy computed tomographic (CT) imaging system or multiple energy electron beam tomography (EBT) system having at least two different energies;
   monitoring characteristics of the cyclically moving body part;
   gating the multiple energy CT imaging system or multiple energy EBT system in accordance with the monitored characteristics of the cyclically moving body part so that acquisitions are acquired at at least two different kVps and a first acquisition in each consecutive cycle starts at a same cardiac phase; and
   utilizing data acquired at the different kVps to generate material decomposition images of the cyclically moving body part.

2. A method in accordance with claim 1 wherein said gating the multiple energy CT imaging system or multiple energy EBT system in accordance with the monitored cyclically moving body part further comprises prospectively triggering the multiple energy (CT) imaging system or multiple energy EBT system in accordance with the monitored cyclically moving body part so that acquisitions acquired in alternate cycles of the cyclically moving body part are acquired at two different kVps, and that acquisitions in alternate cycles are acquired at the same phase of the cyclically moving body part.

3. A method in accordance with claim 2 wherein the cyclically moving body part is a heart, monitoring the cyclically moving body part comprises monitoring an ECG signal from the patient, and further comprising using the material decomposition images for material/tissue discrimination.

4. A method in accordance with claim 3 wherein a temporal resolution of the CT imaging system or multiple energy EBT system is 50 ms or less.

5. A method in accordance with claim 2 wherein said gating the multiple energy CT imaging system or multiple energy EBT system in accordance with the monitored cyclically moving body part further comprises acquiring said acquisitions in alternate cycles so that, at one kVp, a multiphase acquisition is performed, whereas at the other kVp, a single phase acquisition is performed at a cardiac phase included in the multiphase acquisition.

6. A method in accordance with claim 5 wherein the cyclically moving body part is a heart, monitoring the cyclically moving body part comprises monitoring an ECG signal from the patient, and further comprising using the material decomposition images for material/tissue discrimination.

7. A method in accordance with claim 5 further comprising utilizing the data acquired at the different kVps to perform at least one of coronary calcification scoring, an angiogram, a wall motion study, or a cardiac function study.

8. A method in accordance with claim 2 wherein said gating the multiple energy CT imaging system or multiple energy EBT system in accordance with the monitored cyclically moving body part further comprises further comprises performing a first single phase data acquisition at a first kVp followed by a second single phase data acquisition at a second kVp, wherein each acquisition is acquired during the same cycle of the monitored cyclically moving body part but at a different phase.

9. A method in accordance with claim 8 wherein the cyclically moving body part is a heart, monitoring the cyclically moving body part comprises monitoring an ECG signal from the patient, and further comprising using the material decomposition images for material/tissue discrimination.

10. A method in accordance with claim 9 wherein the second single phase data acquisition starts within 50 ms of the first single phase data acquisition.

11. A method in accordance with claim 2 wherein said gating the multiple energy CT imaging system or multiple energy EBT system in accordance with the monitored cyclically moving body part further comprises performing a first single phase data acquisition at a first kVp near an end systole phase of a cardiac cycle of the heart followed by a second single phase acquisition at a second kVp, and performing a third single phase data acquisition at the first kVp after the first and the second single phase data acquisitions, near an end of a diastole phase, followed by a fourth single stage acquisition at the second kVp.

12. A method in accordance with claim 11 wherein the cyclically moving body part is a heart, monitoring the cyclically moving body part comprises monitoring an ECG signal from the patient, and further comprising using the material decomposition images to determine artery calcification.

13. A method in accordance with claim 11 further comprising utilizing data acquired at the different kVps to provide an ejection fraction.

14. A method in accordance with claim 13 wherein a time difference between the first and the second data acquisitions and between the third and the fourth data acquisitions is less than 50 ms.

15. A method in accordance with claim 1 wherein the at least two different kVps are 140 kVp and 90 kVp.

16. A computed tomographic (CT) imaging system or multiple energy electron beam tomographic (EBT) system having a multiple energy x-ray source and detector array configured to scan a portion of a patient including a heart to thereby collect data and to reconstruct material decomposition images of the portion of the patient including the heart utilizing the scanned data, an electrocardiogram (ECG) monitor configured to monitor cardiac phase of the heart to generate an ECG signal representative thereof, said CT imaging system or multiple energy EBT system configured to:
  gate the multiple energy CT imaging system or multiple energy EBT system in accordance with an ECG signal so that acquisitions of data are acquired at at least two different kVps and a first acciuisition in each consecutive cycle starts at a same cardiac phase; and
  utilize the acquired data at the different kVps to generate material decomposition images including images of the heart.

17. A CT imaging system or multiple energy EBT system in accordance with claim 16 wherein to gate the CT imaging system or multiple energy EBT system in accordance with the ECG signal, the CT imaging system or multiple energy EBT system is further configured to prospectively trigger in accordance with the ECG signal so that data acquisitions acquired in alternate cardiac cycles are acquired at two different kVps, and that the data acquisitions in alternate cycles are acquired at the same cardiac phase.

18. A CT imaging system or multiple energy EBT system in accordance with claim 17 wherein said CT imaging system or multiple energy EBT system is further configured to acquire said data acquisitions in alternate cardiac cycles so that, at one kVp, a multiphase data acquisition is performed, whereas at the other kVp, a single phase data acquisition is performed that includes a phase included in the multiphase data acquisition.

19. A CT imaging system or multiple energy EBT system in accordance with claim 16 wherein to gate the CT imaging system or multiple energy EBT system in accordance with the ECG signal, said CT imaging system or multiple energy EBT system is further configured to perform a first single phase data acquisition at a first kVp followed by a second single phase data acquisition at a second kVp, wherein each acquisition is acquired during the same cycle of the monitored cyclically moving body part but at a different phase.

20. A CT imaging system or multiple energy EBT system in accordance with claim 16 wherein to gate the CT imaging system or multiple energy EBT system in accordance with the ECG signal, said CT imaging system or multiple energy EBT system is further configured to perform a first single phase data acquisition at a first kVp near an end systole phase of a cardiac cycle of the heart followed by a second single phase acquisition at a second kVp, and to perform a third single phase data acquisition at the first kVp after the first and the second single phase data acquisitions, near an end of a diastole phase, followed by a fourth single stage acquisition at the second kVp.

* * * * *

UNITED STATES PATENT AND TRADEMARK OFFICE
CERTIFICATE OF CORRECTION

PATENT NO. : 7,236,559 B2  Page 1 of 1
APPLICATION NO. : 11/205556
DATED : June 26, 2007
INVENTOR(S) : Jha et al.

It is certified that error appears in the above-identified patent and that said Letters Patent is hereby corrected as shown below:

In Claim 16, column 14, line 12, delete "acciuisition" and insert therefor -- acquisition --.

Signed and Sealed this

First Day of July, 2008

JON W. DUDAS
*Director of the United States Patent and Trademark Office*